United States Patent [19]

Ray

[11] Patent Number: 5,531,745
[45] Date of Patent: *Jul. 2, 1996

[54] SYSTEM FOR STABILIZING THE SPINE AND REDUCING SPONDYLOLISTHESIS

[75] Inventor: R. Charles Ray, Tacoma, Wash.

[73] Assignee: Danek Medical, Inc., Memphis, Tenn.

[ * ] Notice: The term of this patent shall not extend beyond the expiration date of Pat. No. 5,470,333.

[21] Appl. No.: 339,580

[22] Filed: Nov. 14, 1994

Related U.S. Application Data

[63] Continuation of Ser. No. 31,374, Mar. 11, 1993, abandoned.

[51] Int. Cl.$^6$ ................................................. A61B 17/70
[52] U.S. Cl. ................................................ 606/61; 606/72
[58] Field of Search ........................... 606/61, 60, 69, 606/71, 105, 72, 73; 623/17, 16

[56] References Cited

U.S. PATENT DOCUMENTS

| | | | |
|---|---|---|---|
| 1,025,008 | 4/1912 | Miner | 606/71 |
| 3,604,414 | 9/1971 | Borges | 606/71 |
| 4,246,660 | 1/1981 | Wevers | 606/71 |
| 5,084,049 | 1/1992 | Asher et al. | 606/61 |
| 5,092,893 | 3/1992 | Smith | 623/17 |
| 5,108,395 | 4/1992 | Laurain | 606/61 |
| 5,147,360 | 9/1992 | Dubousset | 606/61 |
| 5,261,907 | 11/1993 | Vignaud et al. | 606/60 |
| 5,261,909 | 11/1993 | Sutterlin et al. | 606/61 |

FOREIGN PATENT DOCUMENTS

| | | | |
|---|---|---|---|
| 1711860 | 2/1992 | U.S.S.R. | 606/61 |
| 780652 | 8/1957 | United Kingdom | 606/61 |

OTHER PUBLICATIONS

"Chopin Plate," Cotrel–Dubousset Instrumentation, SOFAMOR, 6 pp. Date Unknown, Author Unknown.
"Triangulation of Pedicular Instrumentation," Ruland et al. vol. 16 No. 6 Supplement, 1991, S270–S276. Spine.
Posterior Cervical Stablization with Lateral Mass Plate Technique, Haid et al., p. 11. AME, Inc. Surgical Manual, Date Unknown.
"Lateral Mass Posterior Plating and Facet Fusion for Cervial Spine Instability," BNI Quarterly, vol. 7, No. 2, Spring 1991, p. 6. Author Unknown.
"The TSRH™ System: designed with unmatched versaility," Shaping the Future of Spinal Instrumentation, Danek Group, Inc., 1992, p. 3. Author Unknown.

*Primary Examiner*—Guy Tucker
*Attorney, Agent, or Firm*—Woodard, Emhardt, Naughton Moriarty & McNett

[57] ABSTRACT

A system for achieving reduction of curvature of the lumbar region of the spine associated with spondylolisthesis includes transverse plates affixed to vertebrae L4 and L5 and sacral plates affixed to opposite sides of the sacrum. These plates in combination with the longitudinal plate along the posterior anterior plane in which the spinous processes lie allows for effective reduction of the curvature and secure fixation of this region of the spine. The transverse plates include textured surfaces which allow them to mate in a manner which prevents undesirable slippage therebetween. The system is also compact and does not interfere with the paraspinal muscles which run along either side of the spinous processes.

9 Claims, 5 Drawing Sheets

SYSTEM FOR STABILIZING THE SPINE AND REDUCING SPONDYLOLISTHESIS

This application is a continuation of application Ser. No. 08/031.374 filed Mar. 11, 1993, now abandoned.

FIELD OF THE INVENTION

The present invention relates to surgical devices and methods for reducing deformity of the spine, and particularly the lumbar, and holding the spine while a spine fusion heals. While the invention is capable of reducing mild rotational deformity, it particularly relates to the reduction of spondylolisthesis.

BACKGROUND OF THE INVENTION

Spondylolisthesis is a condition of the spine where one vertebrae segment moves forward abnormally both in flexion (rotation) and translation relative to the vertebra immediately below it. This may be due to (a)torn soft tissue restraints (ligaments, joint capsules, etc.), (b) eroded and deformed joints (degenerating spondylolisthesis), or (c) a defect in the bone between the lamina, spinal process and transverse process as one unit and the rest of the vertebrae as a second unit (spondylolytic spondylolisthesis).

When spondylolisthesis is present, the upper vertebral segment moves anteriorly in a saggital plane both in an angular flexion, as well as a straight translational direction. Generally, treatment of spondylolisthesis corrects both types of displacement so that the flexion and translation of the upper element and the relative extension of translation of the lower element are both corrected to restore the normal lordotic alignment of the lumbar spine.

One way to treat spondylolisthesis is to reduce the deformity with a pair of longitudinal plates attached at each level S-1, L-5 and L-4 by means of pedicle screws, (e.g., Roy Camille plates or variable slotted plates (Steppe plates.) Since the pedicle screws are angled medially in line with the long axis of the pedicle, the distance between the tips of the screws and the position where the screw will ultimately attach to the plate is different. Another difficulty with longitudinal plates is aligning multiple screws inserted at different pedicle angles even if no reduction is performed. A third problem is that reducing using only longitudinal plates is much weaker than reducing with two pedicle screws pre-connected with a transverse connecting plate. Longitudinal plates also place a large mass of metal over the facet joints where they restrict the ingrowth of blood vessels into the healing fusion and thus inhibit bone formation. The mass of the plates and screw attachment is also in the middle of the paraspinal muscles (instead of between the muscles) creating more dead space and scar tissue.

It is desirable to have a system for treating spondylolisthesis that provides secure fixation of the lower lumbar region of the spine and effectively reduces the accentuated curvature resulting from spondylolisthesis. Such desirable system would also include a plate design that does not interfere with the paraspinal muscles. Furthermore, it would be desirable if the system would allow for adjustment of the positional relationship between the plates and the pedicle screws so that optimum plate placement could be maintained before, during, and after reduction.

SUMMARY OF THE INVENTION

The present invention relates to a system and the components of such a system for stabilizing the lower lumbar region of the spine and for reducing displacement of vertebrae L4, L5, and the sacrum resulting from the condition known as spondylolisthesis. The system includes instrumentation that achieves the above objectives without interfering with the paraspinal muscles and permits one to maintain an optimum plate position before, during and after reduction.

The system formed in accordance with the present invention includes first and second transverse plates for securing to vertebrae L4, and third and fourth transverse plates for securing to vertebrae L5. The first, second, third, and fourth transverse plates each include at one end a bore for receiving a pedicle screw along a first axis. Extending from the bore in a direction transverse to the first axis are two substantially parallel spaced-apart fingers of substantially equal length. Each pair of spaced-apart fingers include a superior surface and an opposing inferior surface. The inferior surfaces of the spaced-apart fingers of the first and third transverse plates are textured and the superior surfaces of the spaced-apart fingers of the second and fourth transverse plates are textured. The system also includes first and second sacral plates that include a substantially planar body carrying a plurality of bores for rigidly fixing the sacral plates independently to opposite lateral portions of a sacrum. Extending from the body of each sacral plate are two substantially parallel spaced-apart fingers of substantially equal length having superior and opposing inferior surface. The inferior surfaces of the spaced-apart fingers of the first sacral plate are textured and the superior surfaces of the spaced-apart fingers of the second sacral plate are textured. A longitudinal member that includes a superior end and an inferior end connected by elongate spaced-apart members is also part of the system. The superior end, inferior end, and the spaced-apart members define a slot in the longitudinal plate. The longitudinal plate, transverse plates, and sacral plates are secured together by fasteners. The fasteners secure the spaced-apart fingers of the transverse plates and the sacral plates to the longitudinal plate.

The present invention also relates to the individual transverse plates and sacral plates that are components of the system described above. With respect to the transverse plates, either the inferior surface of the spaced-apart fingers or the superior surface of the spaced-apart fingers are textured with a repetitive pattern having an amplitude ranging from about 15 to about 25 thousandths of an inch. Additionally, with the transverse plates, the spaced-apart fingers may be aligned with or offset from the first axis of the bore in accordance with the present invention. With respect to the sacral plates, as with the transverse plates, either the inferior or superior surface of the spaced-apart fingers are textured with a repetitive pattern having an amplitude ranging from about 15 to about 25 thousandths of an inch.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

Figure 1:
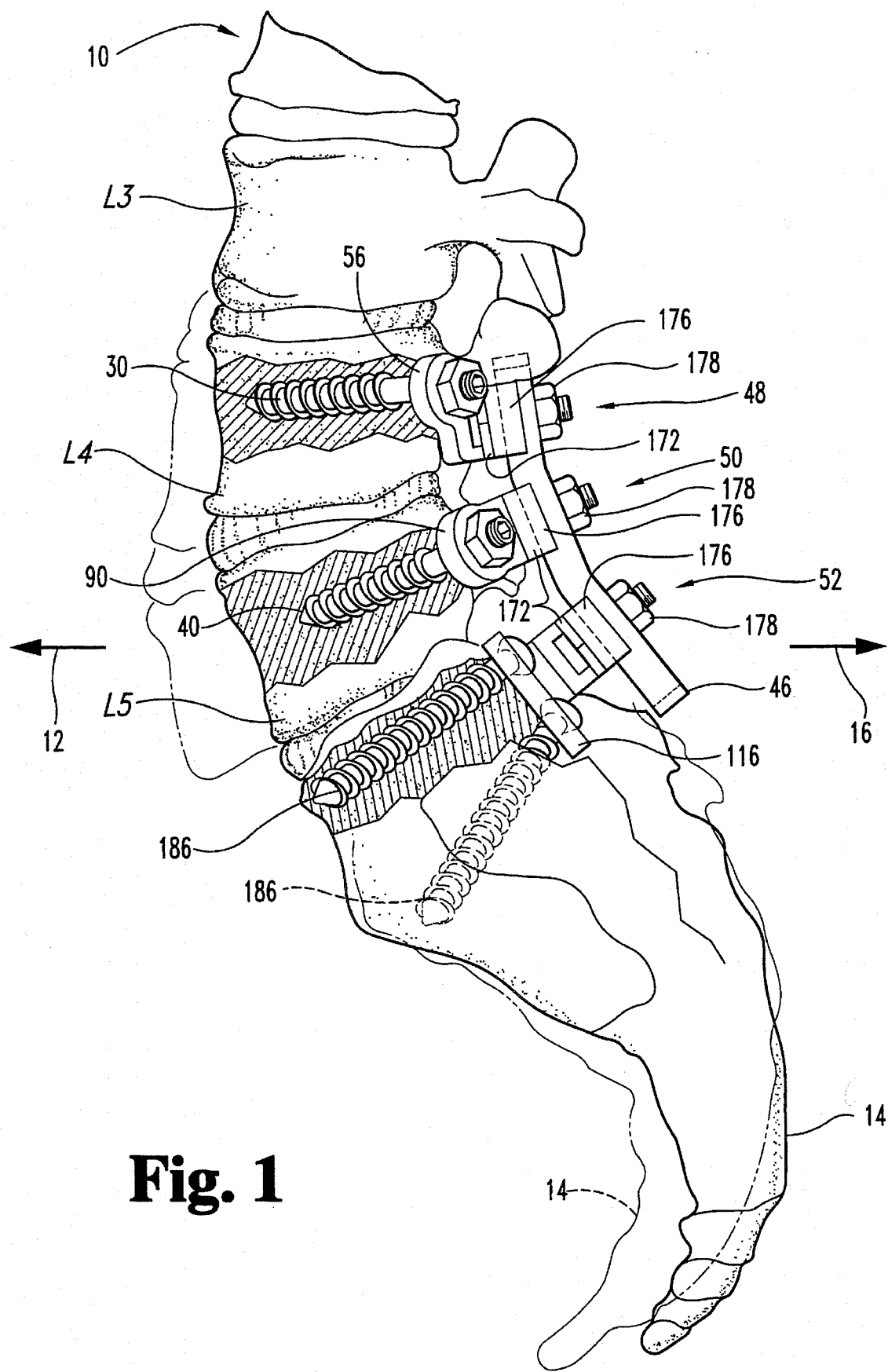
FIG. 1 is an elevational view of the left side of vertebrae L4, L5 and the sacrum with portions of the same being cut away.

Referring to the ghost line depiction in FIG. 1, spondylolisthesis is a condition of the lumbar region of spine 10 wherein the spinous process, lamina, and inferior articular processes of the fifth lumbar vertebrae (and sometimes the fourth lumbar vertebrae) are united together, but separate from the rest of the bone. This condition results in an accentuated curvature in an anterior direction (indicated by arrow 12) of the lumbar region of the spine and displacement of the sacrum in a posterior direction (indicated by arrow 16). As described above, correction of this curvature is achieved by pushing sacrum 14 in the anterior direction and pulling on vertebrae L4 and L5 in posterior direction 16.

Figure 2:
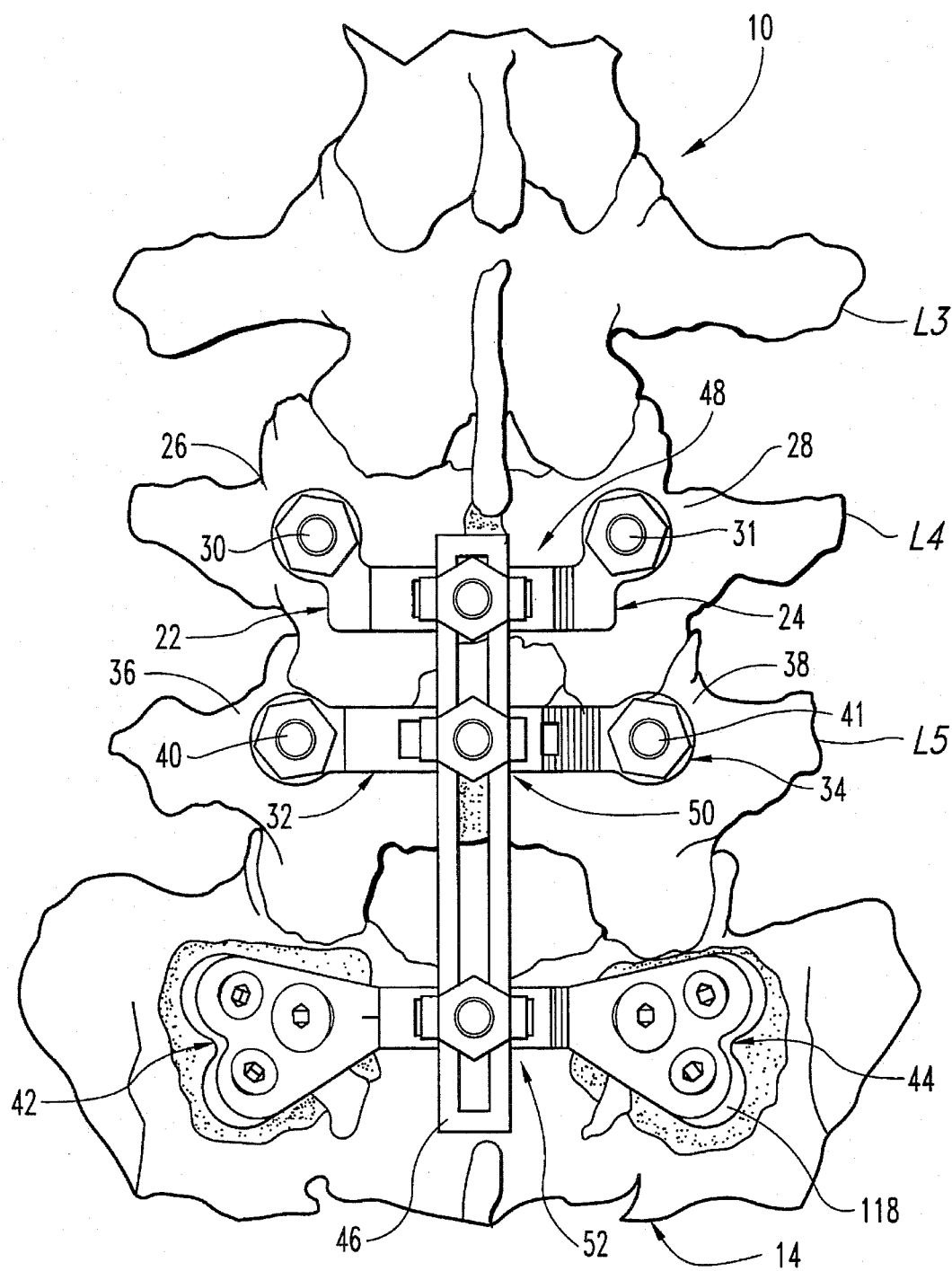
FIG. 2 is an elevational view of the posterior of the lumbar region of the spine with the system formed in accordance with the present invention applied thereto.

Referring additionally to FIG. 2, the system formed in accordance with the present invention for fixating the lumbar region of a spine 10 and reducing spondylolisthesis includes first transverse plate 22 and second transverse plate 24 that are respectively attached to left pedicle 26 and right pedicle 28 of vertebrae L4 with respective pedicle screws 30 and 31. Third transverse plate 32 and fourth transverse plate 34 are respectively attached to left pedicle 36 and right pedicle 38 of vertebrae L5 with respective pedicle screws 40 and 41. The system also includes first sacral plate 42 and second sacral plate 44 that are attached to sacrum 14 adjacent the lumbosacral junction on opposite lateral sides thereof. Positioned along an axis transverse to transverse plates 22, 24, 32, and 34 and sacral plates 42 and 44 is longitudinal plate 46 that is concave in the posterior direction to allow for fixation of the lower lumbar region of spine 10 in the desired position. Transverse plates 22, 24, 32, and 34 and sacral plates 42 and 44 are connected to longitudinal plate 46 by fasteners 48, 50, and 52 that are described below in more detail.

Figure 3:
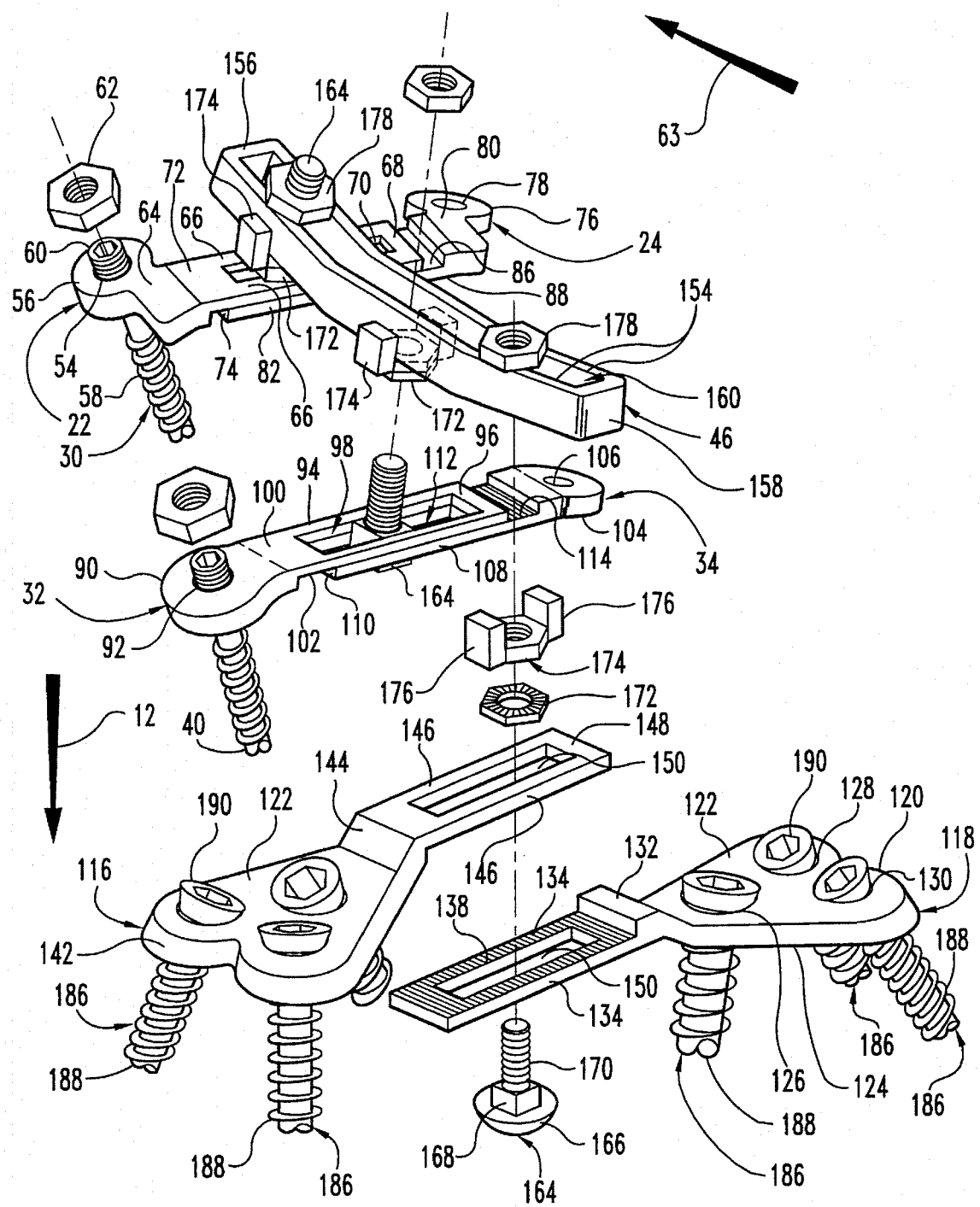
FIG. 3 is an exploded perspective view of the components of the system formed in accordance with the present invention.

Referring specifically to FIG. 3, the individual components making up the system generally described above are illustrated in more detail and described below. First transverse plate 22 includes a bore 54 at left end 56. Left end 56 is rounded and bore 54 is centered therein and is sized to receive pedicle screw 30 along a first axis. Pedicle screw 30 includes a primary threaded portion 58 at one end for insertion into pedicle 26 and a secondary threaded portion 60 at the opposite end for receiving pedicle nut 62 which secures pedicle screw 30 to first transverse plate 22. Extending in the inferior direction (opposite the superior direction 63) from left end 56 is rectangular flange 64. Flange 64 provides an offset element from which elongate spaced-apart fingers 66 extend in a lateral direction substantially transverse to the first axis. Spaced-apart fingers 66 are substantially equal in length and include ends opposite flange 64 that are connected by transverse end member 68. In this manner, flange 64, spaced-apart fingers 66, and end member 68 define a slot 70 that passes through first transverse plate 22. Flange 64 is also canted laterally from right to left in the anterior direction 12 so that the plane in which left end 56 and flange 64 lie is different from the plane in which spaced-apart fingers 66 and end member 68 lie.

Left end 56 and flange 64 have a thickness D measured from posterior surface 72 to anterior surface 74. Spaced-apart fingers 66 and end member 68 have a thickness measured from posterior surface 72 and anterior surface 74 equal to about one-half D. In order to provide the narrow thickness of spaced-apart fingers 66 and end member 68, a portion of anterior surface 74 is removed. For first transverse plate 22, anterior surface 74 of spaced-apart fingers 66 and end member 68 are textured with serrations. The peaks and valleys of the serrations have a repetitive pattern having an amplitude of approximately 15 to 25 thousandths of an inch. Other repetitive patterns can be used provided they help to prevent slippage between first transverse plate 22 and second transverse plate 24 as described below in more detail. In the illustrated embodiment, first transverse plate 22 has been illustrated with an offset provided by flange 64. Alternatively, first transverse plate 22 can be straight like the third and fourth transverse plates described below in more detail.

Continuing to refer primarily to FIG. 3, second transverse plate 24 for vertebrae L4 includes right end 76 that includes bore 78 and flange 80 that are substantially mirror images of left end 56, bore 54, and flange 64 of first transverse plate 22. Accordingly, these features will not be described in any more detail. Second transverse plate 24 differs from first transverse plate 22 in that spaced-apart fingers 82 and transverse end member 84 include posterior surface 86 and anterior surface 88, wherein posterior surface 86 is textured as described above. In order to provide the narrowed thickness of spaced-apart fingers 82 and end member 84, a portion of posterior surface 86 is removed. When textured posterior surface 86 of spaced-apart fingers 82 and end member 84 of second transverse plate 24 and textured anterior surface 74 of spaced-apart fingers 66 and end member 68 of first transverse plate 22 are mated together, slippage therebetween is minimized because of the mating of the textured surfaces.

Continuing to refer primarily to FIG. 3, third transverse plate 32 includes a left end 90 that is a substantially circular plate and includes bore 92 passing perpendicularly therethrough for receiving pedicle screw 40 along a first axis. Pedicle screw 40 is identical to pedicle screw 30 described above. Extending from left end 90 are substantially parallel spaced-apart fingers 94 of substantially equal length. Ends of spaced-apart fingers 94 opposite left end 90 are connected by transverse end member 96. Left end 90 is canted laterally from right to left in an anterior direction so that left end 90 lies in a plane different from a plane in which spaced-apart fingers 94 and end member 96 lie. Left end 90, spaced-apart fingers 94 and end member 96 define a slot 98 passing through third transverse plate 32. Spaced-apart fingers 94 and end member 96 have a thickness in the posterior to anterior direction approximately equal to one-half the thickness of left end 90 in the same direction. Spaced-apart fingers 94 and end member 96 include posterior surface 100 and an opposing anterior surface 102. The reduced thickness of spaced-apart fingers 94 and end member 96 is provided by removing a portion of anterior surface 102. As described above with respect to first transverse plate 22, anterior surface 102 is textured.

Continuing to refer to FIG. 3, fourth transverse plate 34 includes right end 104, that is substantially a mirror image of left end 90 of third transverse plate 32. Right end 104 includes bore 106 that passes through right end 104. Similar to left end 90 of third transverse plate 32, right end 104 is canted laterally from left to right in an anterior direction 12. Fourth transverse plate 34 also includes substantially parallel spaced-apart fingers 108 that extend laterally from right end 104. Spaced apart fingers 108 are substantially equal in length and are connected at an end opposite right end 104 by transverse end member 110. Right end 104, spaced-apart fingers 108, and end member 110 define slot 112 passing through fourth transverse plate 34. As with third transverse plate 32, spaced-apart fingers 108 and end member 110 have a thickness in the posterior to anterior direction that is approximately equal to one-half the thickness of right end 104 in the same direction. This reduced thickness is provided by removing a portion of posterior surface 114 of spaced-apart fingers 108 and end member 110. Fourth transverse plate 34 includes spaced-apart fingers 108 whose posterior 114 is textured with the repetitive pattern described above with respect to the other transverse plates. The repetitive pattern of fourth transverse plate 34 will mate up with the repetitive third transverse plate 32 to prevent slippage therebetween.

Figure 6:
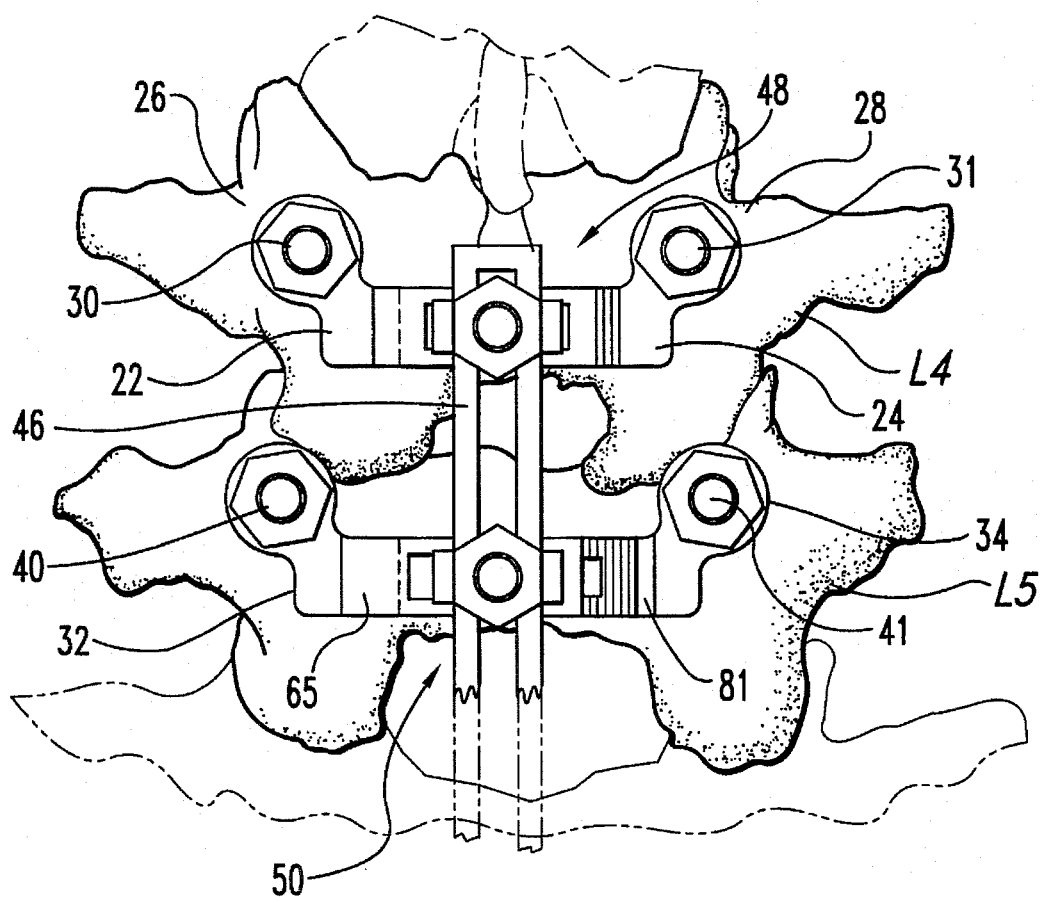
FIG. 6 is an elevational view of the posterior of the lumbar region of a spine with an alternative embodiment of the system formed in accordance with the present invention applied thereto.

As noted above, it should be understood that while first and second transverse plates 22 and 24 described above and illustrated in FIG. 3 include right and left ends and spaced-apart fingers that are offset, a straight-line configuration similar to third and fourth transverse plates 32 and 34 may also be applied if appropriate. Alternatively, as illustrated in FIG. 6, third and fourth transverse es 32 and 34 may include an offset similar to first and second transverse plates 22 and 24. To achieve such offset, first transverse plate 32 is provided with substantially rectangular flange 65 between its left end and the spaced apart fingers, and fourth transverse plate 34 is provided with substantially rectangular flange 81 between its right end and the spaced apart fingers. Flanges 65 and 81 are substantially identical in shape to flanges 64 and 80 described above with respect to FIG. 3.

Figure 5:
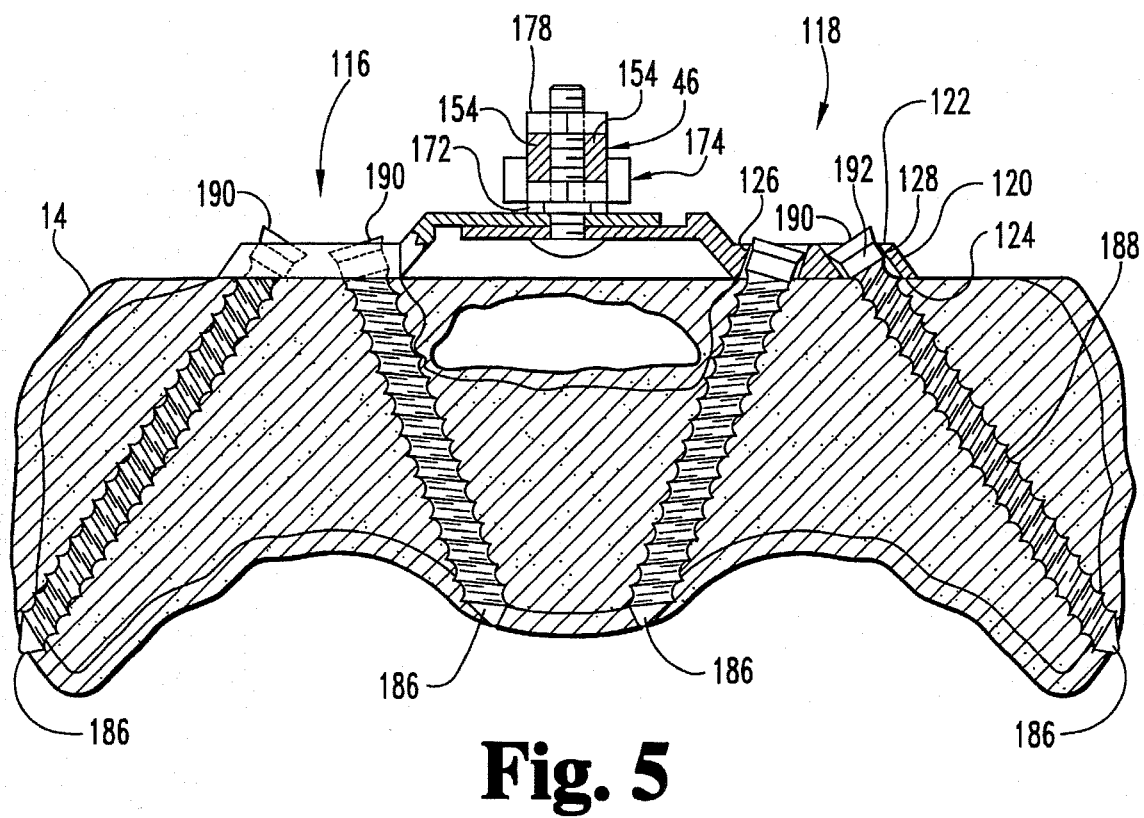
FIG. 5 is a plan view in the inferior direction of the sacrum along line 5—5 in FIG. 2.

Referring to FIGS. 2, 3 and 5, the system formed in accordance with the present invention also includes left sacral plate 116 and right sacral plate 118. In the illustrated embodiment, sacral plates 116 and 118 are illustrated as being triangulated, however, it should be understood that it is not necessary to include triangulated sacral plates and straight sacral plates including only two screws, rather than three could be used. In FIGS. 2 and 3, right sacral plate 116 and left sacral plate 118 are illustrated. Right sacral plate 118 is a mirror image of left sacral plate 116; therefore, only right sacral plate 118 will be described in detail. Right sacral plate 118 has a base 120 having a posterior surface 122 and an opposing anterior surface 124. Anterior surface 124 of sacral plate 118 is designed to intimately contact the posterior surface of the sacrum adjacent the lumbosacral joint. In position, base 120 lies in a plane generally tangential to the portion of the sacrum adjacent to the lumbosacral joint. For purposes of this description, that plane will be referred to as the sacral or dorsal plane. Base 120 of sacral plate 118 carries three bores that extend from the posterior surface of base 120 in a generally anterior direction. These bores are the pedicle bore 126, the lateral bore 128, and the oblique bore 130. The bores 126, 128, and 130, while extending in an anterior direction, are not orthogonal to the sacral plane.

Instead, the pedicle bore 126 has an axis extending in an anterior and medial direction that is offset in the medial direction preferably at an angle of about 15° to a line orthogonal to the sacral plane, although this angle may vary depending upon the particular sacral anatomy being fixed. It is understood that a screw that extends through this bore extends through the pedicle of the sacrum and must always lie within the pedicle.

Lateral bore 128 extends in an anterior and lateral direction that is preferably offset in the lateral direction at an angle of about 30° from a line orthogonal to the sacral plane. If desired, the lateral angle may be varied and the direction of the bore canted in either an inferior or superior direction relative to the sacral plane depending on the sacral anatomy.

Oblique bore 130 passes through base 120 and is offset in the lateral and inferior directions. Bore 130 when viewed in the sacral plane is first preferably offset about 45° from a lateral line, but may be varied depending on the particular sacral anatomy. The bore 130 is also offset in the lateral direction preferably about 30° from a line orthogonal to the sacral plane, but again, may be varied depending upon the particular sacral anatomy.

Extending from the left lateral side of right sacral plate 118 is flange 132. Flange 132 is substantially rectangular and has a thickness in the posterior to anterior direction substantially equal to the thickness of base 120 in the same direction. Flange 132 extends laterally from base 120, in a posterior direction from right to left at an angle of about 45° in the illustrated embodiment. Flange 132 is relatively short with respect to the length of the spaced-apart fingers described below. This angle can be varied depending on the particular sacral anatomy. Extending from the end of flange 132 opposite sacral plate 118 are substantially parallel spaced-apart fingers 134 of substantially equal length. Ends of spaced-apart fingers 134 opposite flange 132 are connected by transverse end member 136. Spaced-apart fingers 134 and end member 136 have a thickness measured in the posterior to anterior direction approximately equal to one-half the thickness of flange 132 or body 120 measured in the same direction. This reduced thickness is provided by removing a portion of the posterior surface 138 of spaced-apart fingers 134 and end member 136. Posterior surface 138 of spaced-apart fingers 134 and end member 136 is also textured with a repetitive pattern in a manner similar to first, second, third, and fourth transverse plates described above. As with the transverse plates, flange 132, end member 136 and spaced-apart fingers 138 define a slot 140 through right sacral plate 118.

Continuing to refer to FIGS. 2, 3 and 5, left sacral plate 116 includes a base 142 and flange 144 that are substantially mirror images of base 120 and flange 132 of right sacral plate 118. Extending from flange 144 are substantially parallel spaced-apart fingers 146 whose ends opposite flange 144 are connected by transverse end member 148. Spaced-apart fingers 146, end member 148 and flange 144 define slot 150 through left sacral plate 116. As with the spaced-apart fingers 134 and the end member 136 of right sacral plate 118, spaced-apart fingers 146 and end member 148 of left sacral plate 116 have a thickness measured in the posterior to anterior direction that is approximately equal to one-half the thickness of flange 144 or base 142 measured in the same direction. Spaced-apart fingers 146 and end member 148 of left sacral plate 116 include an anterior surface 124 that has a portion cut away to provide this thickness. Anterior surface 124 is also textured as described above.

Referring to FIGS. 1, 2 and 3, the illustrated system includes longitudinal plate 46 that includes two spaced-apart elongate members 154 whose inferior end and superior end are connected by transverse members 156 and 158. Transverse end members 156 and 158, and spaced-apart members 154 define a slot 160 through longitudinal plate 46. Longitudinal plate 46 is concave in the posterior direction which provides the curvature needed to successfully treat spondylolisthesis. The plate is bent on the table to the alignment desired as determined by a template bent to match the patient or the final alignment desired. Longitudinal plate 46 is long enough to extend between first transverse plate 22 and second transverse plate 24 on vertebrae L4 and sacral plates 116 and 118 on the sacrum. Longitudinal plate 46 has a thickness measured in the anterior to posterior direction that is substantial enough to provide the rigidity needed for complete fixation and treatment of the spine.

Referring to primarily FIGS. 2, 3, 4 and 5, fasteners 48, 50 and 52 used to secure the transverse plates and the sacral plates to the longitudinal plate are identical except for the differences noted below. Fasteners 48, 50 and 52 include carriage bolt 164, that includes head 166, square flange 168 and threaded portion 170. Flange 168 is located between head 166 and threaded portion 170 and has a thickness that is substantially equal to the combined thickness of the spaced-apart fingers of the first and second transverse plates, or any of the other pairs of plates. Flange 168 has a square cross section orthogonal to the axis of the threaded portion. The lengths of the sides of flange 168 are slightly less than the width of the slots in the transverse plates or sacral plates. Accordingly, a square flange can be positioned within the respective slots and prevented from rotating. Threaded portion 170 is generally long enough to extend through the combined spaced-apart fingers of the respective pairs of plates, the other elements of the fastener described below in more detail, and the posterior surface of the longitudinal plate. Depending on the particular spinal anatomy, fastener 50 may include a threaded portion that is longer than the threaded portions for fasteners 48 and 52. Fasteners 48, 50 and 52 also include a thin primary nut 172 that is threaded to mate with threaded portion 170 on carriage bolt 164. Primary nut 172 includes a posterior and anterior surface, both of which are textured to facilitate secure tightening against the posterior surface of the transverse plates and to prevent slippage between nut 172 and the anterior surface of washer 174 described below. After threaded portion 170 is passed through the slots in a pair of plates, primary nut 172 and carriage bolt 164 are used to secure spaced-apart fingers of the respective pairs of plates together. Fasteners 48, 50 and 52 also include thin washer 174 that has a bore for receiving threaded portion 162 of carriage bolt 164 after primary nut 172 has been seated. Around periphery of washer 174 are two flanges 176 extending in the posterior direction. Flanges 176 are spaced-apart 180° around the periphery of washer 174. The lateral distance between flanges 176 is large enough so spaced-apart members 154 of the longitudinal plate 46 will fit between flanges 176. Flanges 176 extend from washer 174 in a posterior direction, a distance that is less than the thickness of the longitudinal plate measured in the same direction so that the ends of flanges 176 do not extend above longitudinal plate 46 when the system is secured together. After threaded portion 170 is passed through slot 160 in longitudinal plate 56, threaded portion 170 is secured by secondary nut 178 that includes a threaded bore for mating with threaded portion 170.

Figure 4:
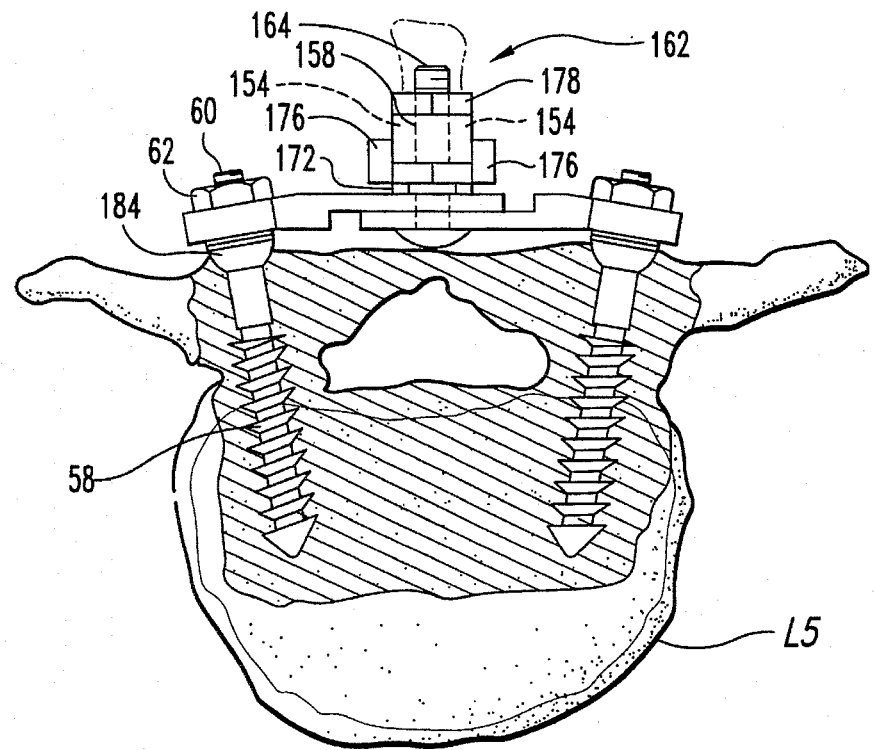
FIG. 4 is a plan view in the inferior direction of vertebrae L5 along line 4—4 in FIG. 2.

Referring to FIGS. 2, 3 and 4, pedicle screws 30, 31, 40, and 41 used to secure first, second, third and fourth transverse plates to vertebrae L4 and L5 include at a lower end a primary threaded portion 58 and at the opposite end a secondary threaded portion 60. Intermediate these threaded portions is a flange 184 having a diameter slightly larger than the diameter of secondary threaded portion 60. Flange 184 terminates at its upper end in a shoulder that is positioned in a plane orthogonal to the axis of the screw. The pedicle screws can be secured into vertebrae L4 or L5 down to flange 184 after which the bore in the transverse plate is passed over the secondary threaded end 60 down to the shoulder of flange 184. The bore is sized just slightly larger than the secondary threaded portion so that the pedicle screw can reciprocate relative to and transverse to the plate, but cannot angulate relative to the screw axis when engaging the bore. A nut 62 is then threaded onto secondary threaded portion 60 and used to tighten the anterior surface of the plate against the shoulder of flange 184. A pedicle screw that can be used in the context of the present invention is available from Danek Group, Inc., Medical Division. To facilitate insertion of the pedicle screw into the pedicle, the end of the pedicle screw adjacent secondary threaded portion 60 includes an indentation for receiving a tool, such as an Allen wrench.

Referring to FIGS. 3 and 5, screws 186 used to affix sacral plates 116 and 118 to the sacrum include a lower threaded portion 188, an upper flared head 190 and a cylindrical section 192 immediately below head 190. Head 190 also carries an Allen socket so that the screw can be rotated into a hole drilled in the pedicle. The bone engaging threads on the lower threaded portion 188 are of conventional design. Cylindrical section 192 has a diameter slightly less than the diameter of the pedicle bore passing through the sacral plates. The diameters are chosen such that when cylindrical section 192 is in the bore, the screw can rotate and reciprocate. However, the tolerances are such that the screw cannot angulate or toggle relative to the axis of the bore. Upper flared head 190 is configured to mate with a countersink provided in the bore when the screw is completely threaded into the sacrum. The same screw is employed in both the lateral bore and the oblique bore.

In use, the system described above can be secured to the lower lumbar region of the spine in accordance with the following steps. It should be understood that differing procedures may be applicable for particular situations and spinal anatomies.

Referring to FIGS. 2 and 3, pedicle screws 30, 31, 40 and 41 are inserted into the pedicles of vertebrae L4 and L5 using conventional techniques. Sacral plates 116 and 118 are secured to a sacrum adjacent the lumbosacral junction with the screws described above. First transverse plate 22 and second transverse 24 plate are loosely mated together by passing threaded portion 170 of carriage bolt 164 through the slots in first plate 22 and second plate 24. The carriage bolt is loosely held in place threading thin nut 172 on exposed threaded portion 170. Bore 78 of second transverse plate 24 is slipped over secondary threaded portion 60 of right pedicle screw 31 and loosely secured thereto with a conventional nut. Bore 54 of first transverse plate 22 is then slipped over secondary threaded end 60 of left pedicle screw 30 and secured loosely thereto with conventional nut 62. Third and fourth transverse plates 32 and 34 are loosely secured to pedicle screws 40 and 41 that have been inserted to vertebrae L5 in a manner similar to that described above with respect to first transverse plate 22 and second transverse plate 24.

With respect to sacral plates 116 and 118, threaded portion 170 of carriage bolt 164 is passed through slots 140 and 150 before the sacral plates are secured to the sacrum. Again, a textured nut 172 is used to loosely secure carriage bolt 164 within slots 140 and 150 of left sacral plate 116 and right sacral plate 118. Sacral plates 116 and 118 are then secured to the sacrum using screws 186. Once the transverse plates and sacral plates are secured to the respective spinal anatomy, textured nuts 172 on carriage bolts 164 can be tightened so that the textured surfaces of the respective spaced-apart fingers come in contact and prevent slippage between the respective plates. Next, flanged washer 174 is slipped over the exposed end of each of the carriage bolts 164 followed by placement of longitudinal plate over the exposed ends of the carriage bolts. Longitudinal plate is then secured to the sacral plates and the transverse plates using the secondary nuts 178 and the exposed portions of the carriage bolts.

Depending on the degree of displacement and curvature resulting from spondylolisthesis, initially the anterior side of longitudinal plate 46 may not contact washer 174 of the fastener for L5. In order to achieve reduction, this gap can be closed by tightening secondary nut 178 on carriage bolt 164. This tightening causes the system to pull on vertebrae L5 and L4 in a posterior direction while pushing on the sacrum in the anterior direction.

In applying the system described above, it should be understood that while the specific transverse plates are designed to avoid various anatomical elements of the lower region of the spine, it may be necessary to remove various anatomical elements in order to achieve placement of the system components. Alternatively, different degrees of offset between the bores for the pedicle screws and the spaced-apart fingers can be used.

In accordance with the present invention, pedicle screws are inserted into the pedicles of vertebrae L4 and L5 so that the pedicle screws are at angles that diverge from each other in the posterior direction. When longitudinal plate is affixed to carriage bolts as described above, before reduction, the distance between the diverging rays associated with the pedicle screws would be fixed, e.g., distance A. After reduction, when vertebrae L4 and L5 are brought into closer proximity with longitudinal bar, the distance between the diverging rays associated with the pedicle screws would be reduced to a distance B, which would be less than A. The system formed in accordance with the present invention provides a means for adjusting for this change in distance between the pedicle screws, which allows one to maintain an optimum plate placement with respect to the plates and the pedicle screws. As the reduction is implemented, the fasteners can be loosened by loosening nut 178 and nut 172. In this manner, the spacing between the individual plates making up the pairs of plates can be adjusted by allowing the textured surfaces to slide over each other. After the desired spacing is achieved, the nuts 172 and 178 can be tightened again to secure the plates together.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A system for stabilizing the lumbar region of the spine and reducing displacement of the spine resulting from spondylolisthesis comprising:

first and second transverse plates for securing to vertebrae L4;

third and fourth transverse plates for securing to vertebrae L5, said first, second, third, and fourth transverse plates each including at one end an eye for receiving a pedicle screw along a first axis and extending from the eye two substantially parallel spaced-apart fingers of substantially equal length, said spaced-apart fingers including a posterior surface and an opposing anterior surface, the anterior surface of said spaced-apart fingers of said first and third transverse plates being textured and the posterior surface of said spaced-apart fingers of said second and fourth transverse plates being textured;

first and second sacral plates, said sacral plates each including a substantially planar body having a plurality of bores for rigidly fixing said sacral plates independently to opposite lateral portions of a sacrum, extending from each body are two spaced-apart fingers of substantially equal length having posterior and opposing anterior surfaces, the anterior surface of the spaced-apart fingers of said first sacral plate being textured and the posterior surface of the spaced-apart fingers of said second sacral plate being textured;

longitudinal member including a superior end and an inferior end connected by spaced-apart members, said superior and inferior end and said spaced-apart members defining a slot in said longitudinal member;

a first fastener for securing the first and second transverse plates to one another and to the longitudinal member, the first fastener extending between the spaced-apart fingers of the first and second transverse plates and between the spaced-apart members of the longitudinal member when fastened;

a second fastener for securing the third and fourth transverse plates to one another and to the longitudinal member, the second fastener extending between the spaced-apart fingers of the third and fourth transverse plates and between the spaced-apart members of the longitudinal member when fastened; and a third fastener for securing the first and second sacral plates to one another and to the longitudinal member, the third fastener extending between the spaced-apart fingers of the first and second sacral plates and between the spaced-apart members of the longitudinal member.

2. The system of claim 1, wherein the textured surfaces of said spaced-apart fingers include a repetitive pattern having an amplitude sufficient to prevent slippage between the textured surfaces when secured together by said fasteners.

3. The system of claim 1, wherein a longitudinal centerline runs parallel to and between the spaced-apart fingers of said first and second transverse plates, said first axis being offset from said centerline such that said longitudinal centerline does not intersect said first axis.

4. The system of claim 1, wherein a longitudinal centerline runs parallel to and between the spaced-apart fingers of said third and fourth transverse plates, said first axis being offset from said centerline such that said centerline does not intersect said first axis.

5. A system for stabilizing the lumbar region of the spine and reducing displacement of the spine resulting from spondylolisthesis comprising:

first and second transverse plates for securing to vertebrae L4;

third and fourth transverse plates for securing to vertebrae L5, said first, second, third, and fourth transverse plates each including at one end an eye for receiving a pedicle screw along a first axis and extending from the eye two substantially parallel spaced-apart fingers of substantially equal length, said spaced-apart fingers including a posterior surface and an opposing anterior surface, the anterior surface of said spaced-apart fingers of said first and third transverse plates being textured and the posterior surface of said spaced-apart fingers of said second and fourth transverse plates being textured;

first and second sacral plates, said sacral plates each including a substantially planar body having a plurality of bores for rigidly fixing said sacral plates independently to opposite lateral portions of a sacrum, extending from each body are two spaced-apart fingers of substantially equal length having posterior and opposing anterior surfaces, the anterior surface of the spaced-apart fingers of said first sacral plate being textured and the posterior surface of the spaced-apart fingers of said second sacral plate being textured;

longitudinal member including a superior end and an inferior end connected by spaced-apart members, said superior and inferior end and said spaced-apart members defining a slot in said longitudinal member; and fasteners for Securing the spaced-apart fingers of said first, second, third, and fourth transverse plates, and the spaced-apart fingers of said first and second sacral plates to said longitudinal member;

a carriage bolt that includes a head, a flange for fitting into said slot, and a threaded portion, said flange located between said head and said threaded portion and having a thickness substantially equal to the combined thickness in a posterior to anterior direction of the spaced-apart fingers of said first and second transverse plates;

a primary nut including a textured posterior surface and an opposing textured anterior surface;

a washer, said washer including an annular body with an outer perimeter and two opposing flanges extending in a posterior direction from opposite edges of said washer; and a secondary nut.

6. A system for stabilizing the lumbar region of the spine and reducing displacement of the spine resulting from spondylolisthesis, comprising:

a first transverse plate adapted for connection to a left pedicle of a first vertebra, the first transverse plate including a first elongated slot therein;

a second transverse plate adapted for connection to a right pedicle of the first vertebra, the second transverse plate including a second elongated slot therein; a third transverse plate adapted for connection to a left pedicle of a second vertebra, the third transverse plate including a third elongated slot therein;

a fourth transverse plate adapted for connection to a right pedicle of the second vertebra, the fourth transverse plate including a fourth elongated slot therein;

a longitudinal member having a longitudinal slot therein;

a first fastener for securing the first and second transverse plates to one another and to the longitudinal member, the first fastener passing through the first, second, and longitudinal slots when fastened;

a second fastener for securing the third and fourth transverse plates to one another and to the longitudinal member, the second fastener passing through the third, fourth, and longitudinal slots when fastened, and wherein the first and second transverse plates include respective first and second textured surfaces, the first and second textured surfaces adapted to engage one another when the first fastener is fastened; and the third and fourth transverse plates include respective third and fourth textured surfaces, the third and fourth textured surfaces adapted to engage one another when the second fastener is fastened.

7. The system of claim 6, wherein the first, second, third and fourth textured surfaces include a repetitive pattern having an amplitude sufficient to substantially prevent slippage between engaged textured surfaces when fastened together by the first and second fasteners.

8. The system of claim 6, further comprising:

a first sacral plate adapted for connection to a left pedicle of a sacrum, the first sacral plate including a fifth slot therein;

a second sacral plate adapted for connection to a right pedicle of the sacrum, the second sacral plate including a sixth slot therein; and a third fastener for securing the first and second sacral plates to one another and to the longitudinal member, the third fastener passing through the fifth, sixth, and longitudinal slots when fastened.

9. The system of claim 6, wherein the first fastener comprises: a first carriage bolt that includes a first head, a first flange for fitting into the first and second slots, and a first threaded portion, the first flange located between the first head and the first threaded portion and having a thickness substantially equal to a combined thickness of the first and second transverse plates;

a first primary nut;

a first washer, the first washer including an annular body having a surface, and two opposing flanges extending in a direction perpendicular to the surface; and a first secondary nut.

* * * * *